United States Patent [19]

Foley et al.

[11] Patent Number: 4,565,862

[45] Date of Patent: Jan. 21, 1986

[54] ETHERS OF ANTIBIOTIC X-14868A

[75] Inventors: Louise H. Foley, Durham, N.H.; Lilian H. Sello; John Westley, both of Cedar Grove, N.J.

[73] Assignee: Hoffmann-La Roche Inc., Nutley, N.J.

[21] Appl. No.: 530,187

[22] Filed: Oct. 24, 1983

Related U.S. Application Data

[63] Continuation-in-part of Ser. No. 444,958, Nov. 29, 1982, abandoned.

[51] Int. Cl.$^4$ ........................ C07H 17/04; A61K 31/71
[52] U.S. Cl. .................................. 536/16.8; 536/18.6; 514/27
[58] Field of Search ............................ 536/18.6, 16.8; 424/180; 514/27

[56] References Cited

U.S. PATENT DOCUMENTS 3,375,243  3/1968  Nevin et al. ..................... 536/18.6
4,223,129  9/1980  Roth et al. ....................... 536/18.6
4,278,663  7/1981  Liu et al. ......................... 536/16.8

*Primary Examiner*—Johnnie R. Brown
*Assistant Examiner*—Elli Peselev
*Attorney, Agent, or Firm*—Jon S. Saxe; Bernard S. Leon; Frank P. Hoffman

[57] ABSTRACT

There is presented compounds of the formula

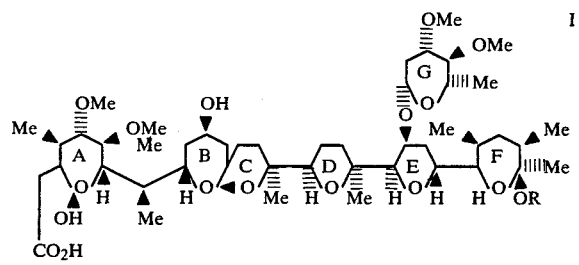

wherein R is $C_2$ to $C_7$ alkyl or lower alkyl hydroxy and their pharmaceutically acceptable salts.

The compounds exhibit activity as antimalarial, anti-inflammatory, anticoccidial and animal growth promotant agents.

Also disclosed is a process to produce said compounds.

8 Claims, No Drawings

ETHERS OF ANTIBIOTIC X-14868A

This application is a continuation-in-part application of U.S. patent application Ser. No. 444,958 filed 11/29/82, abandoned, 10/18/84.

DESCRIPTION OF THE INVENTION

The present invention relates to ethers of antibiotic X-14868A having the formula

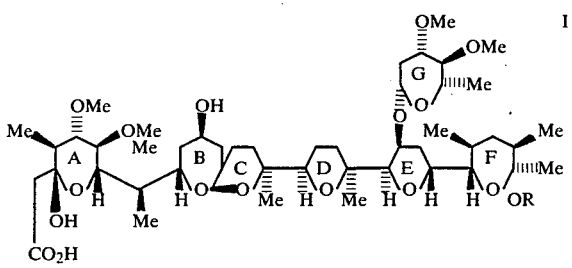

wherein R is lower alkyl or lower alkyl hydroxy and their pharmaceutically acceptable salts.

As utilized herein unless otherwise modified, the term "lower alkyl" shall mean both straight and branched chain ($C_1$ to $C_7$) carbon-hydrogen radicals, preferably $C_2$ to $C_6$ carbon-hydrogen radicals such as ethyl, butyl, hexyl and the like.

The shorthand terminology "Me" in the formula stands for methyl.

The compound X-14868A is a known compound having been disclosed in U.S. Pat. No. 4,278,663, issued July 14, 1981, along with a method of producing the antibiotic utilizing Nocardia sp. X-14868, which is deposited in and is available to the public from the American Type Culture Collection, Rockville, Md. as ATCC 31585. The disclosure of U.S. Pat. No. 4,278,663 is incorporated herein by reference.

The compounds of the present invention are prepared by reacting X-14868A having the formula

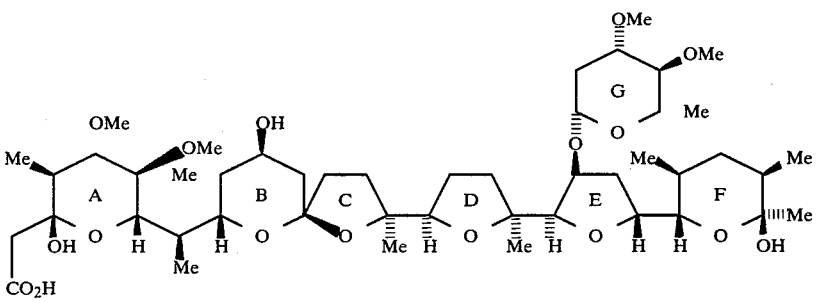

with a primary or secondary $C_1$ to $C_7$ alcohol (wherein R=$C_1$ which is a known compound or R=$C_2$ to $C_7$ alkyl) or a difunctional alcohol, (i.e., a $C_2$ to $C_7$ diol in the presence of an acidic ion exchange resin H+ form such as a sulfonic acid resin H+ form, e.g., DOWEX 50W H+ form. The reaction is run utilizingg the alcohol or diol as the reaction solvent or in an inert solvent at about ambient temperatures, e.g., room temperature.

Examples of suitable alcohols include straight or branched chain $C_2$ to $C_7$ alcohols, e.g., ethyl, n- and iso-propyl, n-butyl, n-hexyl, etc. Examples of suitable diols include difunctional alcohols of $C_2$ to $C_7$ length, such as ethylene glycol, n-butylene glycol, etc.

As utilized herein, where appropriate, both the (R) and (S) configurations of certain ethers are includable within the ambit of the present invention.

The compounds of the present invention exhibit activity as anticoccidial agents. For example, the n-propyl ether and ethyl ether, when tested in two-week old chickens in batteries against mixed Eimeria field isolates, exhibited activity from about twenty (20) to thirty-five (35) ppm. The test consisted of routine laboratory procedures for coccidiosis. Uninfected (UUC) and infected controls (IUC) were utilized. The birds were medicated two days before infection for eight (8) consecutive days. The chickens were infected with 400,000 mixed oocysts of E. acervulina, E. mivati, E. maxima, E. necatrix and E. tenella field strains. There were ten (10) birds per group. The results are shown as follows:

|  | Conc. in feed, ppm | Weight gain, % | % Mort. | Lesion Score | | | |
|---|---|---|---|---|---|---|---|
|  |  |  |  | Upper | Mid | Ceca | Av. |
| UUC | 0 | 100 | 0 | 0.0 | 0.0 | 0.0 | 0.0 |
| IUC | 0 | 48 | 40 | 3.1 | 3.0 | 3.2 | 3.1 |
| ETHYL ETHER of X-14868A | 35 | 73 | 0 | 0.0 | 0.0 | 0.0 | 0.0 |
|  | 25 | 75 | 0 | 0.5 | 0.0 | 0.0 | 0.2 |
|  | 20 | 81 | 0 | 1.5 | 1.5 | 1.6 | 1.5 |
| n-PROPYL ETHER of X-14868A | 35 | 55 | 0 | 0.0 | 0.0 | 0.0 | 0.0 |
|  | 25 | 87 | 0 | 0.1 | 0.0 | 0.0 | 0.03 |
|  | 20 | 72 | 0 | 1.5 | 1.5 | 1.4 | 1.5 |

The compounds of the present invention exhibit activity as antimalarial agents. The ethylene glycyl, n-hexyl, ethyl, n-butyl and n-propyl ethers were tested against chloroquine and pyrimethamine compounds of known antimalarial activity. The compounds were tested twice in an in vitro screen against two strains of Plasmodium falciparum. The activity ($ID_{50}$) is expressed in $\mu g/l$. The results as two values are expressed as follows:

| | Plasmodium falciparum | |
|---|---|---|
| Compound | Strain 13 | T9 clone 96 |
| chloroquine | 390–550 | 44–75 |
| pyrimethamine | 55–61 | 68–70 |
| n-propyl ether of X-14868A | 300–840 | 560–450 |
| ethyl ether of X-14868A | 142–270 | 205–145 |
| n-butyl ether of X-148968A (Na salt) | 500–1200 | 1150–830 |
| ethylene glycyl ether of X-14868A (Na salt) | 39–76 | 48–39 |
| n-hexyl ether of X-14868A (Na salt) |  | 930–650 |
| n-pentyl ether of |  | 1600–800 |

-continued

| Compound | Plasmodium falciparum | |
|---|---|---|
| | Strain 13 | T9 clone 96 |
| X-14868A (Na salt) | | |

A further study evaluating the anticoccidial activity of the 1,3 propanediol ether of antibiotic X-14868A was carried out against mixed Eimeria species in 2-week old chickens housed in batteries. The Eimeria strains utilized in this study were recovered from commercial broiler operations not used in previous studies. For comparison purposes the antibiotics, monensin, lasalocid and antibiotic X-14868A were used. Two-week old Hubbard Cross broiler chickens, obtained from a commercial hatchery and kept in wire-floored electrically heated battery brooders, were used in all studies. Ten birds, selected according to weight and sex (50% female and 50% male) were included in each of three replicates per group. The chickens were medicated two days before infection and maintained on the antibiotic until the termination of the trial, six days post-infection. For each experiment, UUC (uninfected, unmedicated controls) and IUC (infected, unmedicated controls) were used.

Broiler starter mash, a complete feed formula free of drugs, was used as the basal rationl. The medicated feed was prepared by adding to the basal ration the desired concentration of drugs. Each drug concentration was thoroughly mixed into the mash prior to use to provide a uniform blend. In all instances, the medicated feed was fed two days before infection and for a total of eight consecutive days.

The infection was induced by giving orally to each bird a suspension containing *E. acervullna/E. mivati-*—500,000, *E. maxima*—100,000 *E. tenella*—100,000 and *E. brunetti*—50,000 sporulated oocysts properly agitated and suspended in sterile distilled water in amounts of 1.0 ml and inoculated directly into the crop by means of a blunt needle attached to a calibrated syringe.

At the termination of the trials, the surviving birds were sacrificed, necropsied, and scored for gross lesions. All birds that died during the experiments were necropsied. Diagnosis was based on lesion location and morphology. The readings obtained were recorded as average degree of infection (ADI) according to the following scoring system: 0=normal 1=slight, 2=moderate, 3=severe, 4=dead.

In addition, weight gains (%) were recorded.

| Antibiotic | Conc. In Feed, ppm | Weight Gain (%) | Upper | Mid | Ceca | ADI |
|---|---|---|---|---|---|---|
| UUC | 0 | 100 | 0.0 | 0.0 | 0.0 | 0.0 |
| IUC | 0 | 50 | 2.7 | 2.4 | 2.8 | 2.6 |
| 1,3-propanediol | 15 | 71 | 0.0 | 0.0 | 0.0 | 0.0 |
| ether of X-14868A | 12.5 | 81 | 0.0 | 0.0 | 0.07 | 0.02 |
| | 10 | 96 | 0.1 | 0.03 | 0.1 | 0.1 |
| | 7.5 | 91 | 0.7 | 0.3 | 0.5 | 0.5 |
| | 5 | 82 | 1.0 | 0.9 | 1.1 | 1.0 |
| | 2.5 | 59 | 2.3 | 2.1 | 2.2 | 2.2 |
| Antibiotic | 10 | 86 | 0.1 | 0.07 | 0.2 | 0.1 |
| X-14868A | 7.5 | 100 | 0.4 | 0.2 | 0.6 | 0.4 |
| | 5 | 83 | 1.3 | 1.1 | 1.2 | 1.2 |
| Lasalocid | 100 | 99 | 0.5 | 0.5 | 0.9 | 0.6 |
| Monensin | 100 | 80 | 1.1 | 1.1 | 2.0 | 1.4 |

Administration of the antibiotic ethers of X-14868A, hereafter "antibiotics" or "antibiotic compounds" prevents and treats ketosis as well as improves feed utilization in ruminants or swine. The causative mechanism of ketosis is a deficient production of proprionate compounds. A presently recommended treatment is administration of propionate acid or feeds which preferentially produce propionates. It is obvious that encouraging propionate production from ordinary feeds will reduce incidence of ketosis.

It has been found that the ethers of X-14868A increase the efficiency of feed utilization in ruminant animals when they are administered orally to the animals. The easiest way to administer the antibiotics is by mixing them in the animal's feed.

However, the antibiotics can be usefully administered in other ways. For example, they can be incorporated into tablets, drenches, boluses, or capsules, and dosed to the animals. Formulations of the antibiotic compounds in such dosage forms can be accomplished by means of methods well-known in the veterinary pharmaceutical art.

Capsules are readily produced by filling gelatin capsules with any desired form of the desired antibiotics. If desired, the antibiotics can be diluted with an inert powdered diluent, such as a sugar, starch, or purified crystalline cellulose in order to increase their volume for convenience in filling capsules.

Tablets of the antibiotics are made by conventional pharmaceutical processes. Manufacture of tablets is a well-known and highly advanced art. In addition to the active ingredient, a tablet usually contains a base, a disintegrator, an absorbent, a binder, and a lubricant. Typical bases include lactose, fine icing sugar, sodium chloride, starch and mannitol. Starch is also a good disintegrator as is alginic acid. Surface-active agents such as sodium lauryl sulfate and dioctyl sodium sulphosuccinate are also sometimes used. Commonly used absorbents again include starch and lactose, while magnesium carbonate is also useful for oily substances. Frequently used binders are gelatin, gums, starch, dextrin and various cellulose derivatives. Among the commonly used lubricants are magnesium stearate, talc, paraffin wax, various metallic soaps and polyethylene glycol.

The administration of the antibiotic compounds may be as a slow-pay-out bolus. Such boluses are made as tablets except that a means to delay the dissolution of the antibiotics is provided. Boluses are made to release for lengthy periods. The slow dissolution is assisted by choosing a highly water-insoluble form of the antibiotics. A substance such as iron filing is added to raise the density of the bolus and keep it static on the bottom of the rumen.

Dissolution of the antibiotics is delayed by use of a matrix insoluble materials in which the drug is inbedded. For example, substances such as vegetable waxes, purified mineral waxes, and water-insoluble polymeric materials are useful.

Drenches of the antibiotics are prepared most easily by choosing a water-soluble form of the antibiotics. If an insoluble form is desired for some reason, a suspension may be made. Alternatively, a drench may be formulated as a solution in a physiologically acceptable solvent such as a polyethylene glycol.

Suspensions of insoluble forms of the antibiotics can be prepared in nonsolvents such as vegetable oils, e.g., peanut, corn or sesame oil; in a glycol such as propylene glycol or a polyethylene glycol; or in water, depending on the form of the antibiotics chosen.

Suitable physiologically acceptable adjuvants are necessary in order to keep the antibiotics suspended. The adjuvants can be chosen from among the thickeners, such as carboxymethylcellulose, polyvinylpyrrolidone, gelatin, and the alginates. Many classes of surfactants serve to suspend the antibiotics. For example, lecithin, alkylphenol polyethylene oxide adducts, naphthalenesulfonates, alkylbenzesulfonates, and the polyoxyethylene sorbitan esters are useful for making suspensions in liquid nonsolvents.

In addition, many substances which effect the hydrophilicity, density, and surface tension of the liquid can assist in making suspensions in individual cases. For example, silicone anti-foams, glycols, sorbitol, and sugars can be useful suspending agents.

The suspendable antibiotics may be offered to the grower as a suspension, or as a dry mixture of the antibiotics and adjuvants to be diluted before use.

The antibiotics may also be administered in the drinking water of the ruminants. Incorporation into drinking water is performed by adding a water-soluble or water-suspendable form of the antibiotics to the water in the proper amount. Formulation of the antibiotics for addition to drinking water follows the same principles as formulation of drenches.

The most practical way to treat animals with the antibiotic compounds is by the formulation of the compounds into the feed supply. Any type of feed may be medicated with the antibiotic compounds, including common dry feeds, liquid feeds and pelleted feeds.

The methods of formulating drugs into animal feeds are well-known. It is usual to make a concentrated drug premix as a raw material for medicated feeds. For example, typical drug premixes may contain from about 0.1 to about 25 grams of drug per ton of premix. The wide range results from the wide range of concentration of drug which may be desired in the final feed. Premixes may be either liquid or solid.

The formulation of ruminant feeds containing the proper amounts of antibiotic for useful treatment is well understood. It is necessary only to calculate the amount of compound which it is desired to administer to each animal, to take into account the amount of feed per day which the animal eats and the concentration of antibiotic compound in the premix to be used, and calculate the proper concentration of antibiotic compound or of premix, in the feed.

All of the methods of formulating, mixing and pelleting feeds which are normally used in the ruminant feed art are entirely appropriate for manufacturing feeds containing the antibiotic compounds.

As has been shown, oral administration of the antibiotic beneficially alters the production of propionates relative to the production of acetates in the rumen. It may therefore be postulated that the same treatment would also benefit monogastric animals which ferment fibrous vegetable matter in the cecum, since it would be expected that a beneficial change in the propionate/acetate ratio would occur upon oral administration of the instant antibiotic. Horses, swine and rabbits are exemplary animals which digest a part of their food by cecal fermentation.

Determination of volatile fatty acid production

A bovine, surgically modified with a rumen fistula, is used as a source of rumen fluid. The integrity of the rumen is maintained by a rumen cannula (Bar Diamond Labs, Parma, Idaho) which is opened in order to obtain rumen fluid samples. The animal is fed twice daily on 80% concentrate (AHRES ration #39):20% roughage ration. The rumen fluid is obtained prior to the A.M. feeding. The rumen fluid is strained through 4 layers of cheesecloth into a 1 gallon Nalgene container and is kept under anaerobe quality $CO_2$. One thousand mls of the strained rumen fluid are added to 2000 mls of an ice cold buffer based upon that specified by Cheng et al., J. Dair. Sci., 38, 1225 (1955). The composition of this buffer is as follows:

| | | | |
|---|---|---|---|
| $Na_2HPO_4$ | 0.316 g/l | $MgSO_4$ | 0.112 |
| $KH_2PO_4$ | 0.152 | $CaCl_2$ | 0.038 |
| $NaHCO_3$ | 2.260 | $FeSO_4.7H_2O$ | 0.008 |
| NaCl | 0.375 | $ZnSO_4.7H_2O$ | 0.004 |
| KCl | 0.375 | $CuSO_4.5H_2O$ | 0.002 |

The buffered rumen fluid is held in a 1 liter separatory funnel. In order to help maintain the anaerobic character of the rumen fluid and the homogeneity of the buffered rumen fluid, anaerobe quality $CO_2$ is bubbled constantly through the fluid in a separatory funnel beginning approximately $\frac{1}{2}''$ above the separatory funnel stopcock.

One hundred and twenty-five ml Erlenmeyer flasks are used for individual fermentations. Each flask to which a compound will be added contains 0.75 gram of a finely ground 80% concentrate:20% alfalfa hay ration. Flasks which are to be used as drug-free control contain 0.82 grams of the finely ground ration. 0.6 ml of test compound dissolved in an appropriate solvent is added to each flask and allowed to sit overnight. Each compound is examined at a final concentration of 50 ppm. Solvent without test compound is added to drug-free control fermentation flasks. Monensin at 50 ppm is used as a positive control.

Sixty grams of buffered rumen fluid are added to each flask containing test compound and 65.90 grams are added to control flasks. Flasks to which all components have been added are stoppered with a closure fitted with one-way gas valve to permit escape of gases produced by fermentation. Six ml samples are withdrawn from all control flasks as the 0 time samples. Flasks are incubated with shaking (120 oscillations per minute) for 4 hours.

Rumen fluid is poured into 25×150 mm glass tubes and left in an ice bath for approximately 15 minutes to permit settling of particulate matter. The 6 ml quantity of rumen fluid is then added to a 2 ml quantity of 25% (W/V) metaphosphoric acid (J. T. Baker) in 13 ml polycarbonate centrifuge tubes (Autoclear, IEC). Each tube is stoppered and thoroughly mixed. Tubes are left at room temperature for 30 minutes and then centrifuged at 16,000 rpms for 10 minutes in an 874 angle head in an IEC B20 centrifuge. A 1 ml quantity of the internal standard (0.25% 2-methyl valeric acid, Aldrich Chemical Company) is then added to a 4 ml quantity of the supernate. The resulting mixture is filtered through a 0.22 micron Millipore filter using a Swinnex filter and a 5 ml syringe. The filtrate is sealed in one ml glass vials with lined rubber crimp septa.

Each vial, representing each of the individual fermentations, is analyzed by gas liquid chromatography for volatile fatty acids.

Each vial is analyzed by three consecutive on column injections. Concentrations of acetate, propionate, i-butyrate, n-butyrate, i-valerate and n-valerate are calculated by comparison with analyses of a standard solution of VFA's using an internal standardization method.

The activity of the compounds was determined by measuring the relative changes in the production of propionate ($C_3$) and acetate ($C_2$) and n-butyrate ($C_4$), i.e., by the molar VFA ratio $C_3/C_2+C_4$. The increase above control in the ratio ($C_3/C_2+C_4$) obtained with each compound is presented as a percentage of the increase obtained with the positive control. The results are stated in the following table:

| Compound | Molar VFA Ratio $C_3/C_2 + C_4$ | Increase Above Control | % of Increase With Monensin |
|---|---|---|---|
| Untreated Control | .356 | — | — |
| Monensin | .549 | .193 | 100 |
| N—Propyl Ether of X-14868A | .497 | .141 | 73.1 |
| Ethyl Ether of X-14868A | .541 | .185 | 95.9 |
| N—Butyl Ether of X-14868A | .502 | .146 | 75.6 |
| Ethylene Glycyl Ether of X-14868A | .574 | .218 | 113.0 |
| N—Hexyl Ether of X-14868A | .549 | .193 | 100.0 |
| N—Pentyl Ether of X-14868A | .482 | .126 | 65.3 |
| Butylene Glycyl Ether of X-14868A | | .174 | 99.4 |

Molar Ratios of VFA Produced in Fermentations of Compounds at 50 ppm

The salts are prepared from the free acid form of the ethers by methods well-known for compounds of the polyether type in the art; for example, by washing the free acid in solution with a suitable base or salt. Examples of such pharmaceutically acceptable basic substances capable of forming salts for the purpose of the present invention include alkali metal bases, such as sodium hydroxide, potassium hydroxide, lithium hydroxide and the like; alkaline earth metal bases, such as calcium hydroxide, barium hydroxide and the like; and ammonium hydroxide. Alkali metal or alkaline earth metal salts suitable for forming pharmaceutically acceptable salts can include anions such as carbonates, bicarbonates and sulfates.

Examples of organic bases forming pharmaceutically acceptable salts with the polyether compounds are lower alkyl amines and primary, secondary and tertiary hydroxy lower alkylamines such as ethylamine, isopropylamine, diethylamine, methyl-n-butylamine, ethanolamine and diethanolamine.

An amine especially preferred is N-methylglucamine. Salts of N-methylglucamine are of special value because of their water-solubility, which makes them amenable to parenteral use.

The compounds of this invention are typically effective in increasing the efficiency of feed utilization when administered to ruminants orally at rates of from about 0.003 mg/kg/day to about 0.75 mg/kg/day. Most beneficial results are achieved at rates of from about 0.03 mg/kg/day to about 0.075 mg/kg/day.

EXAMPLE 1

Preparation of the ethyl ether of antibiotic X-14868A-free acid

The antibiotic X-14868A-free acid (1.2 g, 0.00128 mol) was dissolved in absolute ethanol (40 ml) and ion exchange resin AG 50W-X4 (200–400 mesh) H+ form (2.0 g, stored overnight under ethanol, filtered and washed with fresh ethanol prior to use) was added. This mixture was stirred at room temperature for 3 hours, and then the resin was filtered off and washed with ethanol. The combined ethanol filtrate was concentrated to a volume of about 10 ml and this solution placed in the cold (0°–5° C.) overnight.

Filtration gave the desired product as white crystals, mp 166°–168° C.

EXAMPLE 2

Preparation of n-propyl ether of antibiotic X-14868A-free acid

The antibiotic X-148686-A free acid (6.2 g, 0.0066 mol) was dissolved in 1-propanol (80 ml) at room temperature and ion exchange resin AG 50W-X4 (200–400 mesh) H+ form (6.0 g, stored under 1-propanol overnight, filtered and washed with 1-propanol prior to use) was added. The resulting mixture was stirred at room temperature for 4 hours or until TLC (ether, hexane, methanol, acetone, NH$_4$OH in a 7:3:0.5:1:0.02 ratio) showed the reaction to be complete.

The resin was filtered off and washed with 1-propanol. The combined filtrates were concentrated first on the rotovap and finally on the pump to give the desired product as a white foam. A sample was crystallized from the minimum amount of 1-propanol, mp 109°–111° C. dec.

EXAMPLE 3

Preparation on n-butyl ether of antibiotic X-14868A-Na salt 1 g of antibiotic X-14868A-Na salt was dissolved in 20 ml of n-butyl alcohol while stirring at room temperature. To this solution, 5 g of AG50W-X4 (200–400 mesh) H+ form resin-previously soaked overnight in n-butyl alcohol, filtered and washed with n-butyl alcohol—was added. The reaction mixture was stirred for 4 hours at room temperature.

Reaction mixture was filtered, fitrate was concentrated in vacuo, residue was dissolved in ethyl acetate and was washed with Na$_2$CO$_3$ solution (saturated at room temperature), followed by H$_2$O wash and was dried over Na$_2$SO$_4$. After filtration and concentration, the residue was crystallized from acetonitrile by the addition of water. Mp. 146°–150° C.

EXAMPLE 4

Preparation of n-butyl ether of antibiotic x-14868-Na salt 1 g of antibiotic X-14868A-Na salt was dissolved in 20 ml n-butyl alcohol while stirring at room temperature. To this solution 5 g of AG50W-X4 (200–400 mesh) H+ form resin—previously soaked overnight in n-butyl alcohol, filtered and washed with n-butyl alcohol—was added. The reaction mixture was stirred overnight at room temperature. The reaction mixture was filtered, concentrated in vacuo, residue was dissolved in methylene chloride and was washed with Na$_2$CO$_3$ (saturated at room temperature), followed by H₂O wash and was dried over Na₂SO₄. After filtration, the solution was concentrated and chromatographed on 200 g silica gel, prepared in methylene chloride, and eluted with 1 liter methylene chloride, 3 liters diethyletherhexane-acetone (7:3:1), followed by 2 liters diethylether-acetone (7:3). Fractions containing the reaction product were concentrated and crystallized from acetonitrile by the addition of water. Mp 155° C.

EXAMPLE 5

Preparation of n-amyl ether of antibiotic X-14868A-Na salt

The n-amyl ether of antibiotic X-14868A-Na salt was prepared as described in Example 3 but using n-amyl alcohol in place of n-butyl alcohol. Mp. 136°-140° C.

EXAMPLE 6

Preparation of n-hexyl ether of antibiotic X-14868A-Na salt

The n-hexyl ether of antibiotic X-14868A-Na salt was prepared as described in Example 3 but using n-hexyl alcohol in place of n-butyl alcohol. Mp. 137°-139° C.

EXAMPLE 7

Preparation of ethyleneglycol ether of antibiotic X-14868A-Na salt 6 g of X-14868A-Na was dissolved in minimal volume of methylene chloride/acetone. Ethylene glycol (100 ml) was added and 30 g of AG50W-X4 (200-400 mesh) H+ resin (resin was previously soaked overnight in ethylene glycol), and the reaction mixture was stirred overnight at room temperature. Water was added to the reaction mixture, resin was filtered out and filtrate was extracted three times with diethylether. Ethereal phase was washed in turn with H₂O, Na₂CO₃, H₂O and was dried over Na₂SO₄. Solvent phase was removed in vacuo and residue was crystallized from acetonitrile by the addition of water. Mp. 162°-165° C.

EXAMPLE 8

Preparation of ethyleneglycyl ether of antibiotic X-14868A-K salt

The ethylene glycyl ether of antibiotic X-14868A-K salt was prepared as described in Example 7 but using KOH in place of Na₂CO₃ and drying the ethereal extract of the reaction mixture by filtering through a celite bed. Mp. 158°-162° C.

EXAMPLE 9

Preparation of 1,4-butyleneglycyl ether of antibiotic X-14868A-Na salt 1,4-butyleneglycyl ether of antibiotic X-14868A-Na salt was prepared as described in Example 7 except that 1,4-butanediol was used in place of ethyleneglycol. The product is a white (amorphous) foam. $[\alpha]_D^{25} = 27.7°$ in CHCl₃, c=1%

EXAMPLE 10

2-Propanol ether of antibiotic-X-14868A free acid

The ionophore antibiotic X-14868A sodium salt (1.1 g) was dissolved in 2-propanol (50 ml) at room temperature and ion exchange resin AG 50W-X4 (200-400 mesh) H+ form (1.1 g stored under 2-propanol, filtered and washed with 2-propanol prior to use) was added to this mixture and stirred at room temperature for 24 hours. The resin was filtered and washed with fresh isopropyl alcohol. The filtrate was concentrated first on the rotovap and finally on the pump to leave a white foam. Microanalysis Calcd for C₅₀H₈₆O₁₇: C, 62.61; H, 9.09; C, 62.73; H, 8.81.

EXAMPLE 11

Preparation of 1,3-propanediol (trimethyleneglycol)ether of antibiotic X-14868A-Na salt Five grams of antibiotic X-14868A-Na salt was dissolved in 100 ml 1,3-propanediol (trimethylene glycol) while stirring at room temperature. To this solution 20 g of AG502-X8 (200-400 mesh) H+ form resin-previously soaked overnight in trimethylene glycol, filtered and washed with trimethylene glycol was added. The reaction mixture was stirred for 3 hours at room temperature. Water was added to the reaction mixture, resin was filtered out and filtrate was extracted twice with diethylether. The pooled ethereal phase was washed in turn with H₂O, Na₂CO₃, H₂O and was dried over Na₂SO₄. Solvent phase was concentrated to an oil and was chromatographed on 200 g silica gel, prepared in methylene chloride, and eluted with 1 liter diethylether-hexane (7:3), 2 liters diethylether-hexane-acetone (7:3:1) 1 liter ethyl acetate-acetone (8:2) followed by 1 liter ethyl acetate-acetone (6:4). Fractions containing the reaction product were pooled and solvent was removed in vacuo yielding a white foam. Microanalysis: Calc. for C₅₀H₈₅NaO₁₈·½H₂O (1006.23)-Calc. C59.68; H 8.62; Na 2.29; H₂O 0.90. Found: C 59.91; H 8.76; Na 2.08; H₂O 1.02; $[\alpha]_D^{25}$ 24.3° in CHCl₃, c=1%.

EXAMPLE 12

Preparation of (S) and (R) 3-hydroxybutyl ether of antibiotic X-14868A-Na salt

The (S) and (R) 3-hydroxybutyl ether of antibiotic X-14868A-Na salt was prepared as described in Example 11, but using 10 g antibiotic X-14868A-Na salt and 1,3-butanediol in place of trimethyleneglycol. Fractions 106-113 of the silica gel chromatography yielded a white foam, the (S) 3-hydroxybutyl ether of X-14868A-Na salt. Microanalysis: Calc. for C₅₁H₈₇NaO₁₈ (1011.25). Calc. C 60.58; H 8.67; Na 2.27. Found: C 60.52; H 8.62; Na 2.29; $[\alpha]_D^{25}$ 28.3° in CHCl₃ c=1%. Fractions: 126-170 of the silica gel chromatography yielded a white foam, the (R) 3-hydroxybutyl ether of antibiotic X-14868A-Na salt. Microanalysis: Calc. for C₅₁H₈₇NaO₁₈ (1011.25). Calc. C60.58; H 8.67; Na 2.27. Found: C 60.08; H 8.99; Na 2.07; $[\alpha]_D^{25}$ 25.9° in CHCl₃, c=1%.

Identity of the (S) and (R)-3-hydroxybutyl ether of antibiotic X-14868A-Na salt was confirmed by using 98% pure (S)- and (R)-1,3-butanediol respectively for the reaction and comparison on TLC.

EXAMPLE 13

Preparation of 5-hydroxypentyl ether of antibiotic X-14868A-Na salt

The 5-hydroxypentyl ether of antibiotic X-14868A-Na salt was prepared as described in Example 11 but using 10 g antibiotic X-14868A-Na salt and 1,5-pentanediol in place of trimethylene-glycol. There was yielded a white foam, 5-hydroxypentyl ether of antibiotic X-14868A-Na salt. Microanalysis: Calculated for $C_{52}H_{89}NaO_{18}$ (1025.27) Calc. C 60.92; H 8.75; Na 2.24. Found: C 60.78; H 8.95; Na 2.14; $[\alpha]_D^{25}$ 25.7° in $CHCl_3$, C=1%.

EXAMPLE 14

Preparation of 1,2-propanediol ether of antibiotic X-14868A-Na salt

Following the procedure of Example 11 but utilizing 1,2-propanediol instead of 1,3-propanediol there is obtained the 1,2-propanediol ether of antibiotic X-14868A.

What is claimed:

1. A compound of the formula:

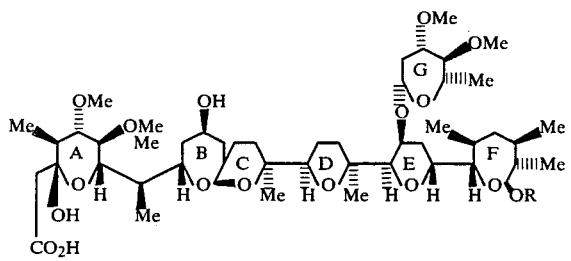

wherein R is lower alkyl hydroxy and the pharmaceutically acceptable salts thereof.

2. A compound of claim 1 selected from the group consisting of the ethyleneglycyl ether, 1,3 or 1,2-propanediol ether, (S) or (R)-3-hydroxybutyl ether, 5-hydroxypentyl ether, or the 1,4-butyleneglycyl ether of antibiotic X-14868A and the pharmaceutically acceptable salts thereof.

3. A compound: the ethyleneglycyl ether of antibiotic X-14868A and its pharmaceutically acceptable salts.

4. A compound: 1,4-butyleneglycyl ether of antibiotic X-14868A and its pharmaceutically acceptable salts.

5. A compound: the 1,3-propanediol ether of antibiotic X-14868A and its pharmaceutically acceptable salts.

6. A compound: the (S)-3-hydroxybutyl ether of antibiotic X-14868A and its pharmaceutically acceptable salts.

7. A compound: the (R)-3-hydroxybutyl ether of antibiotic X-14868A and its pharmaceutically acceptable salts.

8. A compound: the 1,2-propanediol ether of antibiotic X-14868A and its pharmaceutically acceptable salts.

* * * * *